(12) United States Patent
Xu et al.

(10) Patent No.: US 10,849,650 B2
(45) Date of Patent: Dec. 1, 2020

(54) TRANSPERINEAL NEEDLE GUIDANCE

(71) Applicant: ZMK Medical Technologies Inc., Grass Valley, CA (US)

(72) Inventors: Guangyao Xu, Rocklin, CA (US); Rajesh Venkataraman, Rocklin, CA (US); Saradwata Sarkar, Rocklin, CA (US); Michael Ahmadi, Durham, NC (US)

(73) Assignee: EIGEN HEALTH SERVICES, LLC

(*) Notice: Subject to any disclaimer, the term of this patent is extended or adjusted under 35 U.S.C. 154(b) by 1005 days.

(21) Appl. No.: 15/203,417

(22) Filed: Jul. 6, 2016

(65) Prior Publication Data
US 2017/0020558 A1 Jan. 26, 2017

Related U.S. Application Data

(60) Provisional application No. 62/189,352, filed on Jul. 7, 2015.

(51) Int. Cl.
*A61B 8/00* (2006.01)
*A61B 17/34* (2006.01)
(Continued)

(52) U.S. Cl.
CPC ........ *A61B 17/3403* (2013.01); *A61B 8/0841* (2013.01); *A61B 8/12* (2013.01);
(Continued)

(58) Field of Classification Search
CPC ... A61B 17/3403; A61B 8/5246; A61B 8/483; A61B 8/463; A61B 8/4263; A61B 8/4218; A61B 8/4209; A61B 90/11; A61B 8/466; A61B 8/0841; A61B 8/12; A61B 2017/00274; A61B 2017/3411; A61B 2090/3782; A61B 2034/2059;
(Continued)

(56) References Cited

U.S. PATENT DOCUMENTS 3,002,375 A 10/1961 Moffatt et al.
3,415,548 A 12/1968 Goodman et al.
(Continued)

FOREIGN PATENT DOCUMENTS

WO 2007045810 A2 4/2007
WO 2007147232 A1 12/2007
(Continued)

*Primary Examiner* — Joel Lamprecht
(74) *Attorney, Agent, or Firm* — Snell & Wilmer L.L.P.; Russell T. Manning

(57) ABSTRACT

A combined imaging probe holder and interventional needle guide assembly is provided. The imaging probe holder supports an imaging device (e.g., ultrasound probe) in a known relationship with a biopsy/treatment device holder such that a delivery element or interventional needle is constrained within an imaging field of the imaging device. Constraining the biopsy treatment device within the imaging field allows for real-time monitoring of the biopsy/treatment device during insertion of the interventional needle into patient tissue. In addition, the biopsy/treatment device holder is angularly positionable relative to the image field to allow advancement of the delivery element to any desired location within the imaging field.

16 Claims, 13 Drawing Sheets

(51) Int. Cl.
  *A61B 8/12* (2006.01)
  *A61B 8/08* (2006.01)
  *A61B 90/11* (2016.01)
  *A61N 5/10* (2006.01)
  *A61B 18/00* (2006.01)
  *A61B 90/00* (2016.01)
  *A61B 18/14* (2006.01)
  *A61B 18/02* (2006.01)
  *A61B 34/20* (2016.01)
  *A61B 17/00* (2006.01)

(52) U.S. Cl.
  CPC .......... *A61B 8/4209* (2013.01); *A61B 8/4218* (2013.01); *A61B 8/4263* (2013.01); *A61B 8/463* (2013.01); *A61B 8/466* (2013.01); *A61B 8/483* (2013.01); *A61B 8/5246* (2013.01); *A61B 90/11* (2016.02); *A61N 5/1027* (2013.01); *A61B 8/4455* (2013.01); *A61B 18/1477* (2013.01); *A61B 2017/00274* (2013.01); *A61B 2017/3405* (2013.01); *A61B 2017/3411* (2013.01); *A61B 2017/3413* (2013.01); *A61B 2018/00547* (2013.01); *A61B 2018/0293* (2013.01); *A61B 2034/2059* (2016.02); *A61B 2090/365* (2016.02); *A61B 2090/3782* (2016.02); *A61B 2090/3784* (2016.02); *A61N 5/1049* (2013.01); *A61N 2005/1012* (2013.01); *A61N 2005/1058* (2013.01)

(58) Field of Classification Search
  CPC ........ A61B 2018/0293; A61B 18/1477; A61B 2090/3784; A61B 2018/00547; A61B 2017/3413; A61B 2017/3405; A61B 8/4455; A61B 2090/365; A61N 5/1027; A61N 2005/1058; A61N 5/1049; A61N 2005/1012
  See application file for complete search history.

(56) References Cited

U.S. PATENT DOCUMENTS

| | | | |
|---|---|---|---|
| 5,170,790 A | 12/1992 | Lacoste et al. | |
| 5,230,623 A | 7/1993 | Guthrie et al. | |
| 5,282,472 A | 2/1994 | Companion et al. | |
| 5,398,690 A | 3/1995 | Batten et al. | |
| 5,427,108 A | 6/1995 | Bollinger | |
| 5,487,388 A | 1/1996 | Rello | |
| 5,494,039 A | 2/1996 | Onik et al. | |
| 5,824,007 A | 10/1998 | Faraz et al. | |
| 5,971,929 A | 10/1999 | Sakamoto et al. | |
| 6,046,727 A | 4/2000 | Rosenberg et al. | |
| 6,171,249 B1 | 1/2001 | Chin et al. | |
| 6,179,262 B1 | 1/2001 | Ellard et al. | |
| 6,246,200 B1 | 6/2001 | Blumenkranz et al. | |
| 6,261,234 B1 | 7/2001 | Lin | |
| 6,301,989 B1 | 10/2001 | Brown et al. | |
| 6,325,760 B1 | 12/2001 | Takanori et al. | |
| 6,360,027 B1 | 3/2002 | Hossack et al. | |
| 6,378,376 B1 | 4/2002 | Derman et al. | |
| 6,423,009 B1 | 7/2002 | Downey et al. | |
| 6,425,865 B1 | 7/2002 | Salcudean et al. | |
| 6,447,447 B1 | 9/2002 | Mitsumori | |
| 6,451,027 B1 | 9/2002 | Cooper et al. | |
| 6,454,781 B1 | 9/2002 | Witt et al. | |
| 6,620,111 B2 | 9/2003 | Stephens et al. | |
| 6,752,753 B1 | 6/2004 | Hoskins et al. | |
| 6,931,745 B2 | 8/2005 | Granger | |
| 7,008,373 B2 | 3/2006 | Staianovici et al. | |
| 7,108,660 B2 | 9/2006 | Stephens et al. | |
| 7,189,246 B2 | 3/2007 | Otsuka et al. | |
| 7,244,234 B2 | 7/2007 | Ridley et al. | |
| 7,255,310 B2 | 8/2007 | Niwa et al. | |
| 7,287,310 B2 | 10/2007 | Zuzelo | |
| 7,412,776 B2 | 8/2008 | Iikubo et al. | |
| 7,472,615 B2 | 1/2009 | Mayeaux | |
| 7,475,602 B2 | 1/2009 | Molenaar et al. | |
| 7,832,114 B2 | 11/2010 | Suri et al. | |
| 7,942,060 B2 | 5/2011 | Suri et al. | |
| 9,913,596 B2 * | 3/2018 | Krieger | G01R 33/287 |
| 2003/0014039 A1 * | 1/2003 | Barzell | A61B 8/12 606/1 |
| 2003/0018232 A1 * | 1/2003 | Elliott | A61M 37/0069 600/1 |
| 2003/0171678 A1 * | 9/2003 | Batten | A61B 8/0833 600/443 |
| 2005/0075536 A1 | 4/2005 | Otsuka et al. | |
| 2005/0159676 A1 | 7/2005 | Taylor et al. | |
| 2007/0043291 A1 | 2/2007 | Fidel et al. | |
| 2008/0004481 A1 | 1/2008 | Bax et al. | |
| 2008/0064960 A1 | 3/2008 | Whitmore et al. | |
| 2008/0177139 A1 | 7/2008 | Courtney et al. | |
| 2008/0221453 A1 * | 9/2008 | Suri | A61B 8/12 600/459 |
| 2008/0249403 A1 | 10/2008 | Suri et al. | |
| 2008/0269604 A1 | 10/2008 | Boctor et al. | |
| 2009/0030339 A1 | 1/2009 | Cheng et al. | |
| 2009/0145249 A1 | 6/2009 | Dubbeldam et al. | |
| 2010/0036245 A1 | 2/2010 | Yu et al. | |
| 2013/0116548 A1 * | 5/2013 | Kumar | A61B 8/0841 600/424 |
| 2014/0309524 A1 * | 10/2014 | Vetter | A61B 18/149 600/424 |
| 2015/0031990 A1 * | 1/2015 | Boctor | A61B 8/483 600/424 |
| 2015/0065886 A1 | 3/2015 | Stoianovici et al. | |

FOREIGN PATENT DOCUMENTS

| | | |
|---|---|---|
| WO | 2014098766 | 6/2014 |
| WO | 2017007875 | 1/2017 |

* cited by examiner

2D Image Storage

3D Volume Image

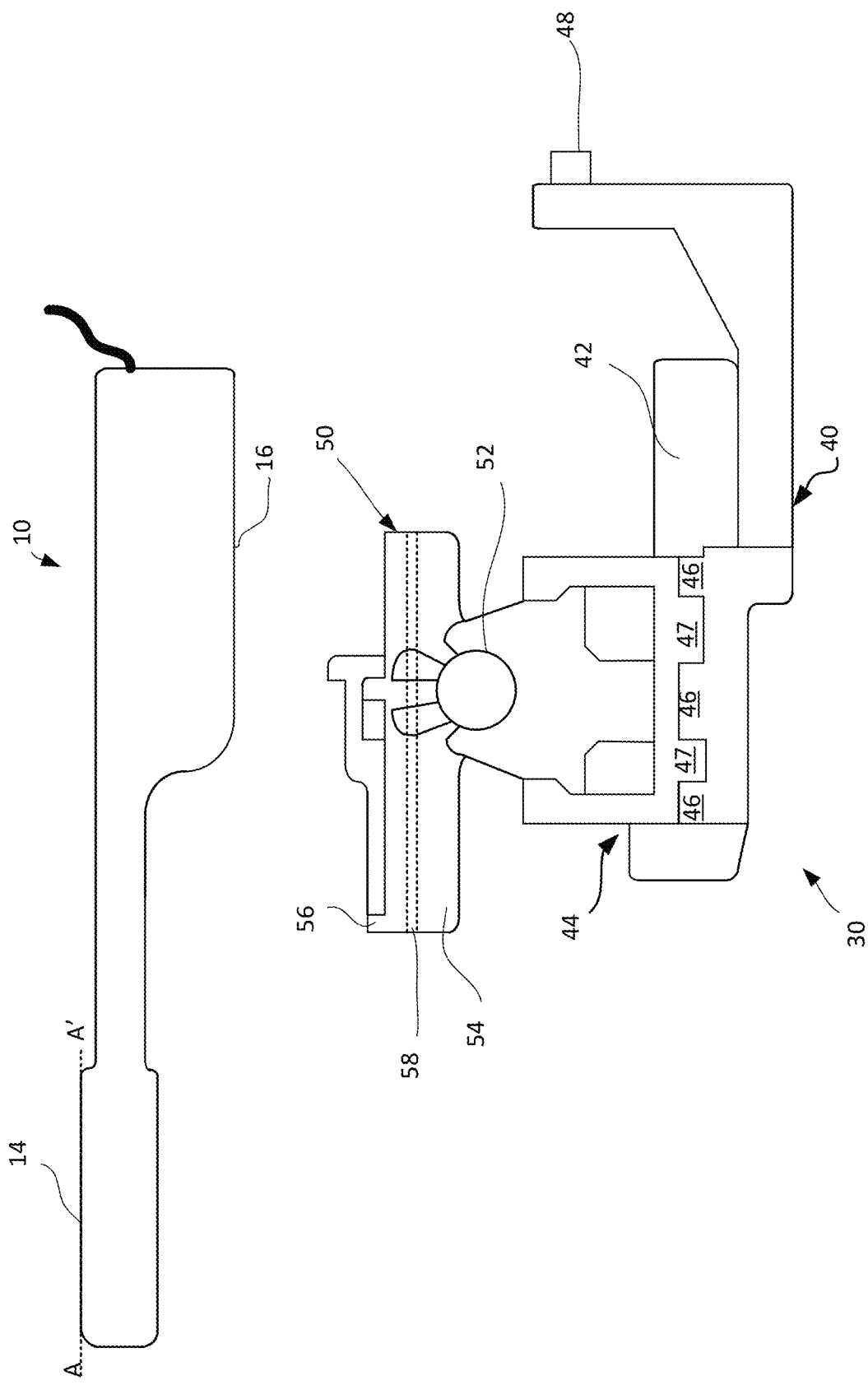

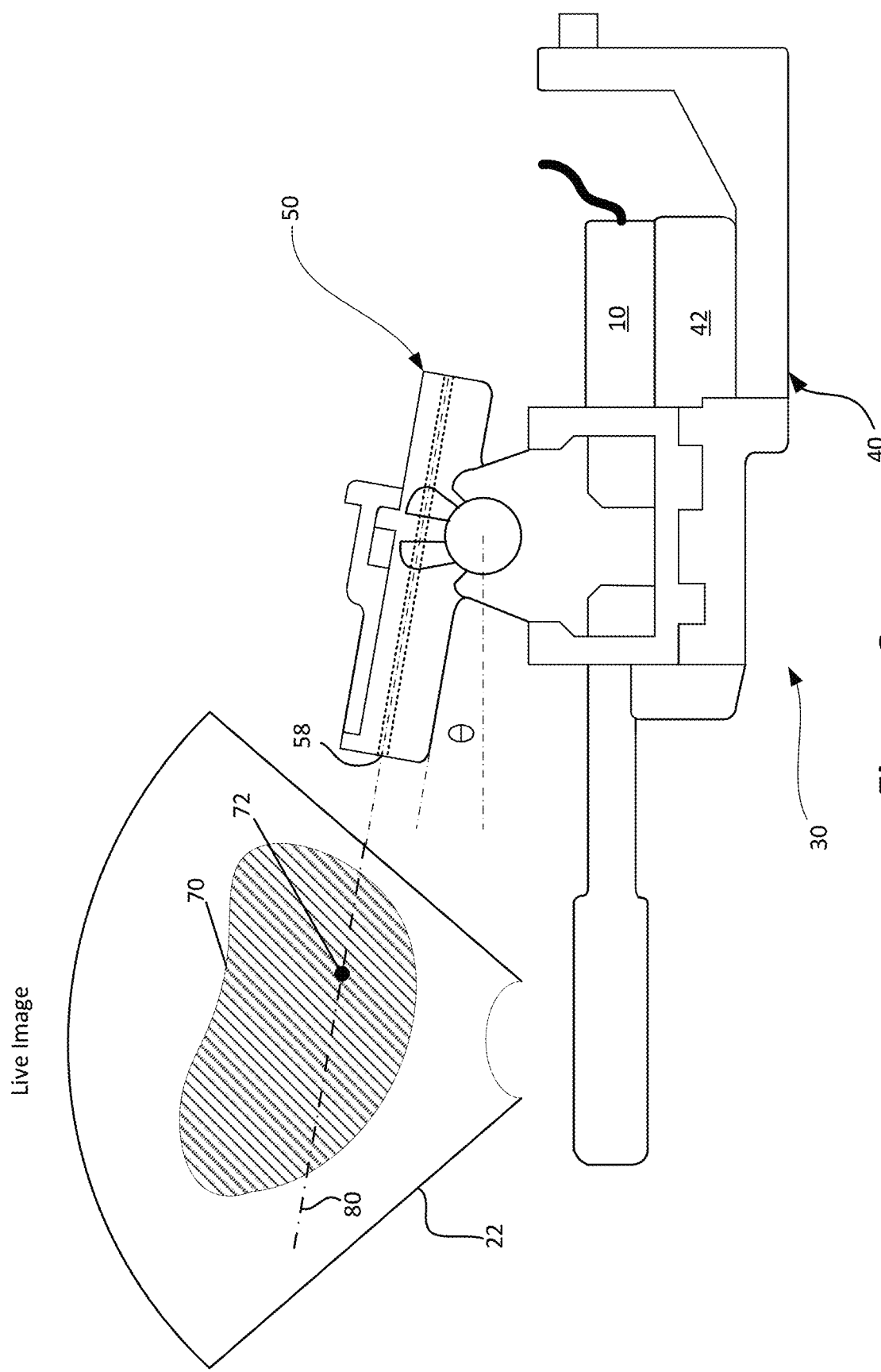

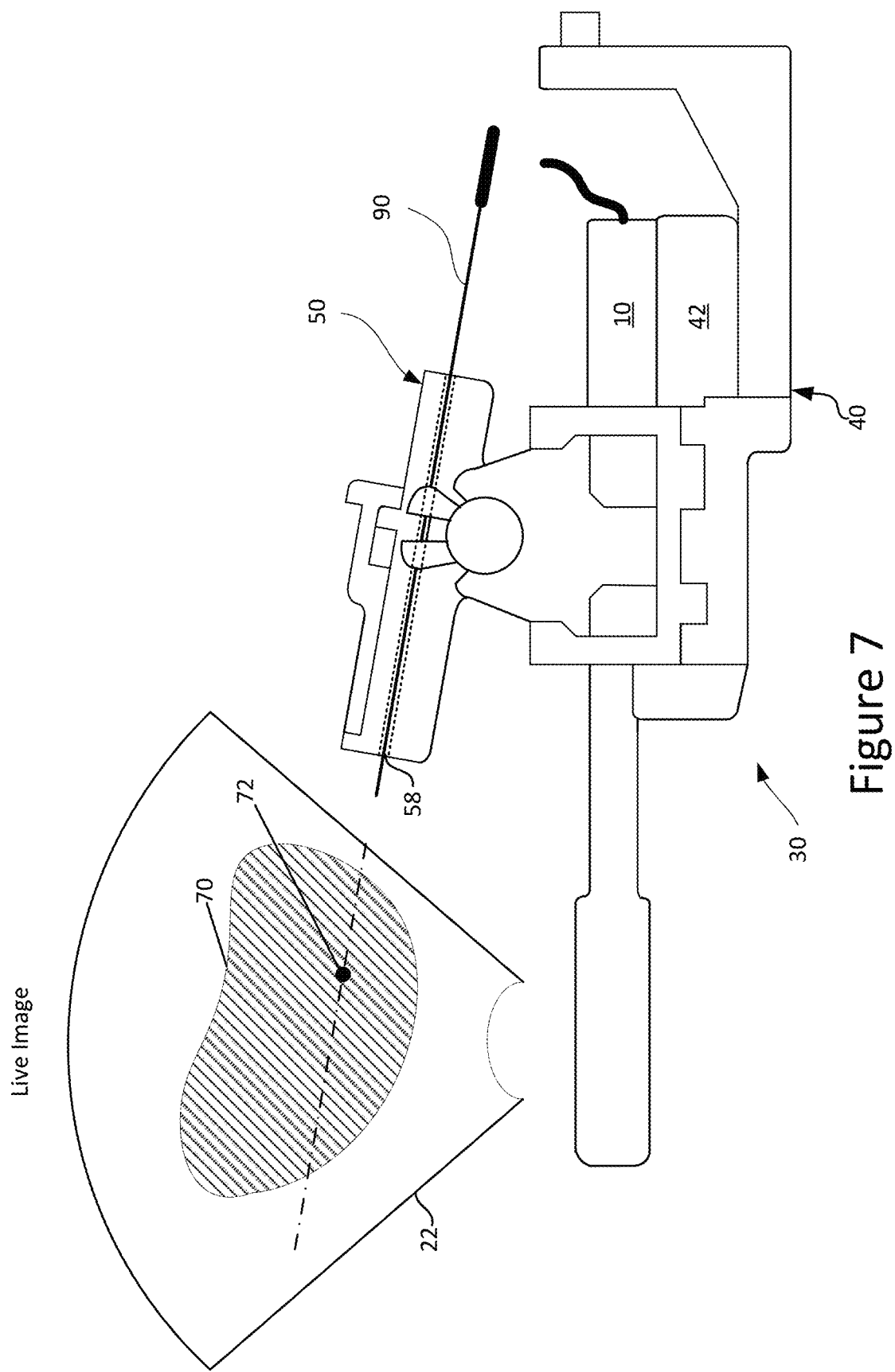

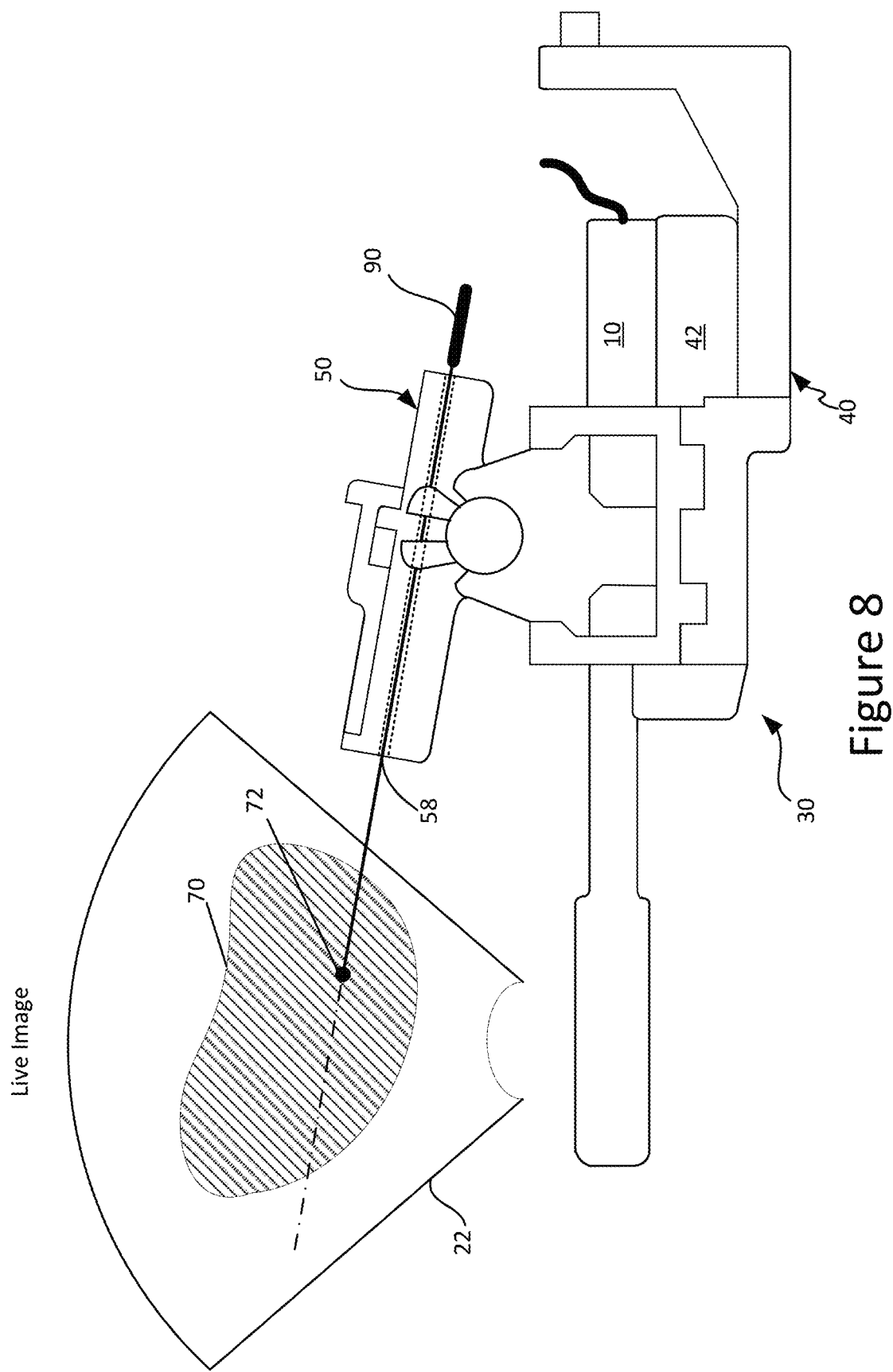

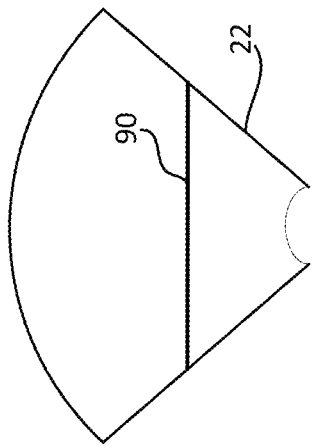
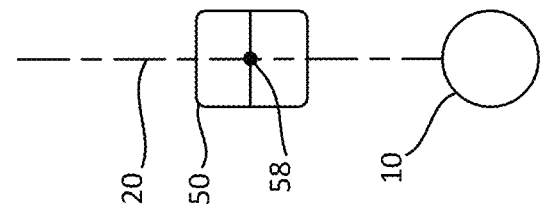
Figure 9D
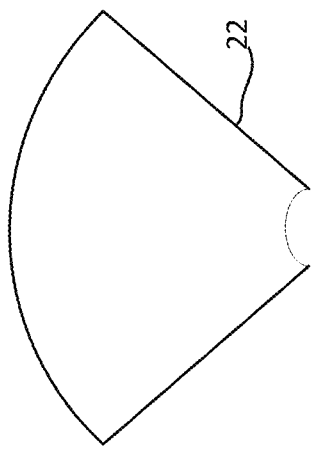
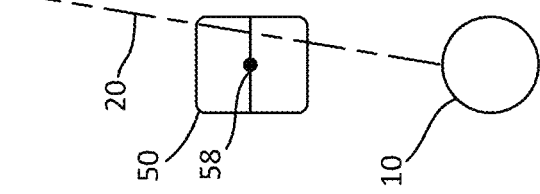
Figure 9C
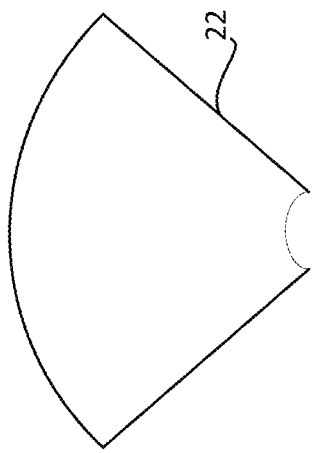
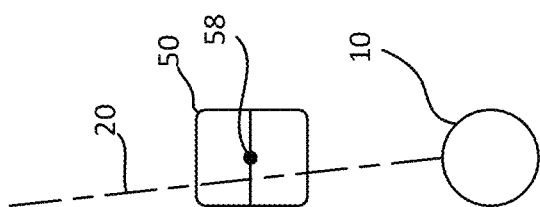
Figure 9B

TRANSPERINEAL NEEDLE GUIDANCE

CROSS REFERENCE

The present application claims the benefit of the filing date of U.S. Provisional Application No. 62/189,352 having a filing date of Jul. 7, 2015, the entire contents of which is incorporated herein by reference.

FIELD

The present disclosure is directed to systems, methods and apparatuses (i.e., utilities) that allow for tracking and guiding interventional needles or needle-like applicators (e.g., biopsy needles, therapy devices) through the patient's rectum or perineum. More particularly, the disclosure relates to utilities that allow for guiding and maintaining a medical imaging instrument along with a needle guidance device in a fixed positional relationship to each other allowing for real-time guidance of any interventional needle through either the patient's rectum or perineum to a desired target location.

BACKGROUND

Doctors and other medical professionals often utilize medical imaging instruments to conduct non-invasive examinations. That is, medical imaging instruments, including X-ray, magnetic resonance (MR), computed tomography (CT), ultrasound, and various combinations of these instruments/techniques are utilized to provide images of internal patient structure for diagnostic purposes as well as for interventional procedures. Such medical imaging instruments allow examination of internal tissue that is not readily examined during normal visual or tactile examination which could then be used for either diagnosis (e.g. MRI for prostate) or for guidance to a region of interest in the body (e.g. interventional procedures like biopsies, therapy, etc.).

Medical imaging devices typically allow for generating 3-D images of internal structures of interest. Such 3-D imaging may improve the accuracy and/or reliability of medical diagnosis. For instance, a medical imaging device may be utilized to generate a 3-D model or map of the prostate such that one or more biopsies may be taken from certain desired locations of the prostate and/or therapy may be delivered to those desired locations of the prostate. For purposes of prostate imaging, a transrectal ultrasound-imaging device (TRUS) provides image acquisition and guidance. TRUS probe is the most widely accepted technique for prostate applications due to its simplicity, high specificity, and real time nature. In such an application, the TRUS probe or similar medical imaging device may be inserted into the rectum of a patient to generate an image. Such images may be utilized to generate a 3D image of the prostate that may subsequently be utilized to take one or more biopsies from a prostate location of interest and/or apply therapy (e.g., implant radioactive seeds) at one or more desired locations.

Traditionally, a medical practitioner has manipulated a medical imaging instrument by hand for medical image acquisition and/or treatment. That is, the medical practitioner manually guides the instrument. Such manual manipulation is suitable for many medical procedures. However, in instances where it is desirable to obtain multiple 2D images for 3-D image generation, manual manipulation of the device may result in significant movement between images. Further, for procedures that require precision like, for example, targeted biopsy and other treatment procedures it is desirable that the relative location between an imaging instrument and an anatomical area of interest be known. That is, it is important that the device directs the imaging instrument to point to a particular tissue location and remain stationary to allow for guiding a biopsy/treatment device to that tissue location within the imaging field. Relative movement between the imaging device and the tissue area of interest during imaging and/or biopsy/treatment may impede the successful performance of these procedures.

Accordingly, a number of holding and manipulating/positioning assemblies have been proposed wherein a holder interfaces with an imaging device such as a TRUS probe. The holder is then interconnected to one or more mechanical armatures and/or actuators such that the probe may be mechanically positioned and/or rotated relative to an area of interest on a patient (a "tracking assembly"). Such systems have allowed for the generation of accurate 3D models from 2D images.

SUMMARY

Provided herein are apparatuses, systems and methods (e.g., utilities) that combine the positioning and support of an imaging device (e.g., ultrasound probe) with a biopsy/treatment device holder such that a delivery element (e.g., interventional needle, trocar, etc.) held by the biopsy/treatment device for insertion into patient tissue is constrained within an imaging field of the imaging device. Constraining the biopsy treatment device within the imaging field allows for real-time monitoring of the biopsy/treatment device during insertion into patient tissue. In addition, the biopsy/treatment device holder is angularly positionable relative to the image field to allow advancement of the delivery element to any desired location within the imaging field. The delivery element/interventional needle may be used to take biopsies and/or apply therapeutic matter such as, for example, brachytherapy seeds, cryoablation fluid, ablation energy, and/or electroporation energy (electric field energy). In one arrangement, movement of the biopsy/treatment device holder is limited to a single degree of freedom allowing angular positioning of a delivery element within a two-dimensional image plane.

According to a first aspect, a utility includes a combined imaging probe (e.g., ultrasound transducer) holder and a biopsy/treatment device holder or 'guidance assembly'. The imaging probe holder generally forms a recessed surface or cradle is configured to receive and secure a portion of an imaging device/probe. In such an arrangement, an acquisition portion (e.g., transducer array) of the imaging device is secured in a known relationship to the probe holder. The probe holder includes a rotatable coupling adapted for rotatable connection with a positioning device such that the probe holder and supported imaging device are operative to rotate about a rotational axis of the positioning device. The positioning device includes various encoders that output a 3D position and orientation of the attached probe holder and supported imaging device. As an acquisition portion (e.g., axis) of the imaging device is known relative to the probe holder, the orientation of the acquisition portion of the imaging device is known in a 3D space of the positioning device. This allows for placing images (e.g., image planes) from the imaging device in the known 3D space. In one arrangement, the acquisition axis of an ultrasound probe is aligned with the rotational axis of the positioning device.

In addition, the utility includes an attached guidance assembly having a guide bore (e.g., needle guide bore) that is aligned with an image plane of the imaging device, when the imaging device is secured within the probe holder. Thus, the spatial relationship of the needle guidance assembly is known relative to the acquisition axis or field of the imaging device. In this regard, a trajectory (e.g., needle trajectory) of the guide bore may be plotted on an output image of the imaging probe. Thus, the imaging probe may be rotated to image a desired portion of an anatomical internal structure having, for example, a target location (e.g., prostate lesion). At this time, an image (e.g., two dimensional image plane) including the target location may be generated on a display. Further, the trajectory of the guide bore (e.g., needle trajectory) may be superimposed on the image. To permit aligning the needle trajectory with the target location, the guide assembly may rotate relative to the cradle to adjust the needle trajectory relative to the image plane. Thus, the needle trajectory may be aligned with a target location within the image. At this time, a user may extend a needle or other delivery element through the guide bore of the guidance assembly into the patient and to the target location. Such of insertion may be provided under real-time imaging.

BRIEF DESCRIPTION OF THE DRAWINGS

FIG. 4A illustrates one embodiment of a probe holder and needle guidance assembly and an ultrasound probe.

FIG. 6 illustrates an angular offset of the needle guidance assembly relative to the probe holder/cradle.

FIG. 7 illustrate a needle inserted in the needle guidance assembly of FIG. 6.

FIG. 8 illustrates the needle of FIG. 7 inserted into a patient under real-time imaging.

FIGS. 9B-9D illustrate one calibration technique.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging, biopsy and therapy, it should be expressly understood that aspects of the present invention may be applicable to other medical imaging applications. In this regard, the following description is presented for purposes of illustration and description.

Systems and methods are disclosed that facilitate obtaining medical images and/or performing medical procedures. One embodiment provides a combined medical imaging device holder (e.g., probe holder) and guidance assembly. The guidance assembly maintains a trajectory of a supported delivery element (e.g., needle, trocar, therapy device, etc.), which adapted for insertion into patient tissue, within an image field/plane of an imaging device (e.g., two-dimensional image plane of an ultrasound probe) held by the probe holder. The probe holder is configured for rotational attachment with a positioning device allowing the location of the imaging device and its imaging plane to be known in a 3D space. The positional relationship between the probe holder and the guidance assembly is maintained while the probe-cradle assembly is rotated. In this regard, the imaging probe supported by the probe holder may obtain multiple 2D or 3D images of a prostate or other anatomical structure in different orientations. The attached guidance assembly may be utilized to direct a needle or other delivery element through the patient's tissue to a location of interest within an image plane of the imaging device. For example, a biopsy needle may be directed through the guidance assembly, through a patient's perineum and into the patient's prostate. As the trajectory of the needle is aligned with the image plane of the imaging probe, the progression of the needle may be displayed on a real-time image of the imaging device such that targeting may be performed under real-time image guidance.

Figure 1A:
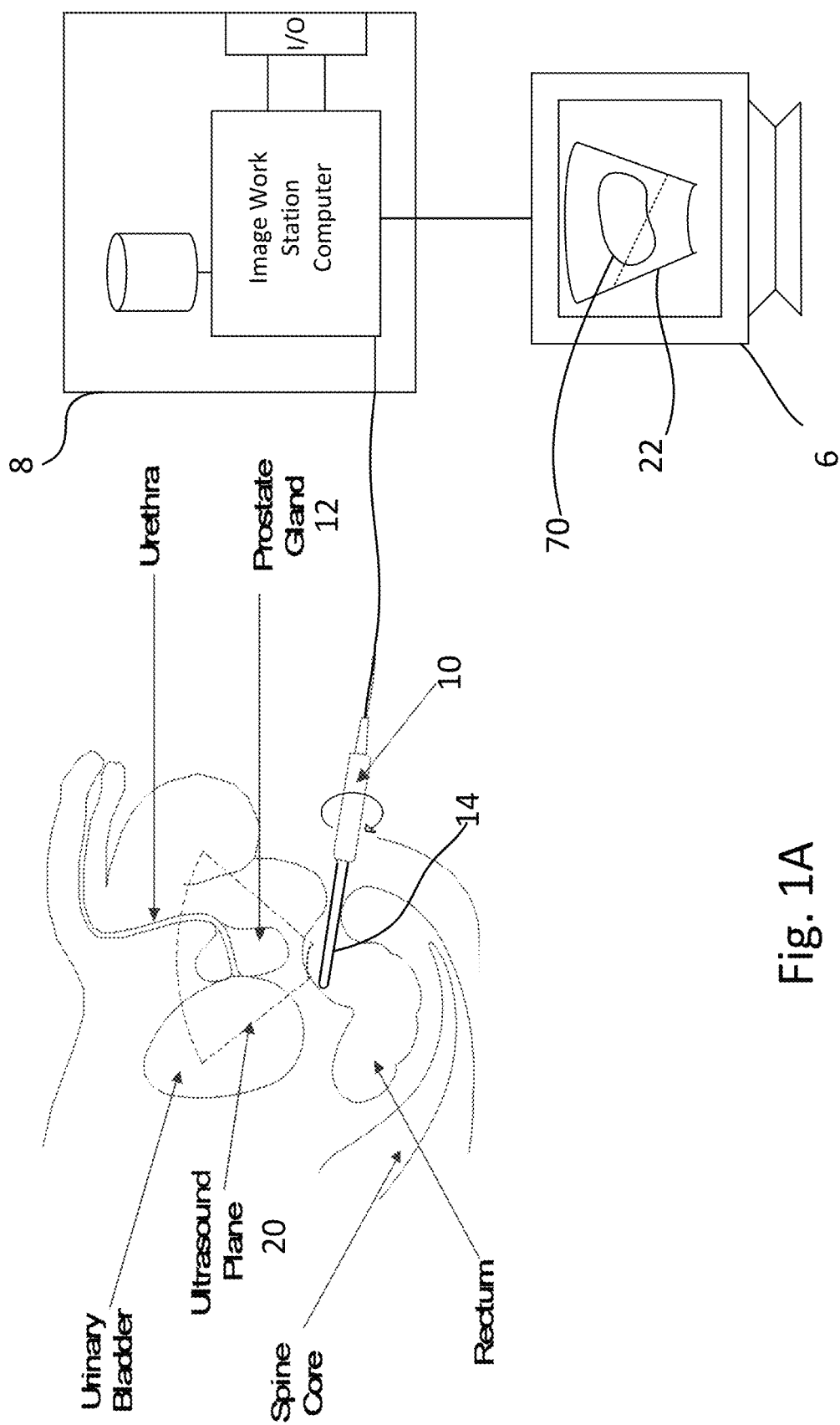
FIG. 1A shows a cross-sectional view of a trans-rectal ultrasound imaging system as applied to perform prostate imaging.
Figure 2A:
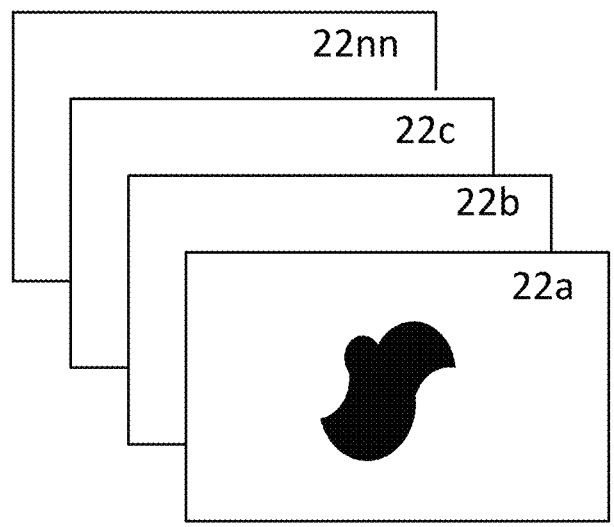
FIG. 2A illustrates two-dimensional images generated by the trans-rectal ultrasound imaging system of FIG. 1.
Figure 2B:
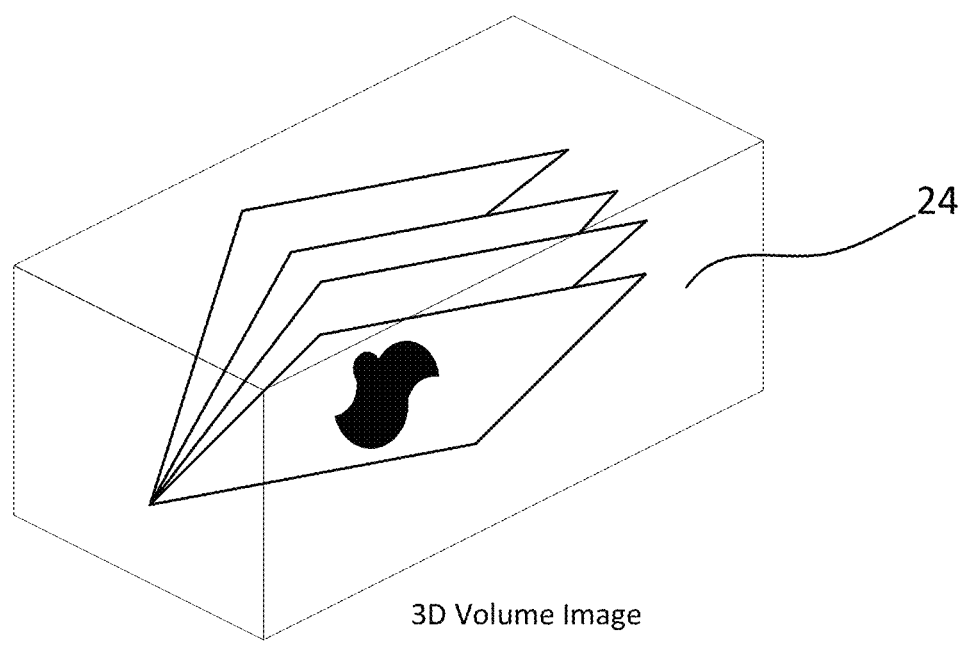
FIG. 2B illustrates a three-dimensional volume image generated from the two dimensional images of FIG. 2A.

FIG. 1A illustrates a transrectal ultrasound probe 10 being utilized to obtain a plurality of 2D ultrasound images of the prostate 12. The illustrated probe 10 scans an area of interest along an imaging plane 20. In such an arrangement, a user may rotate the acquisition portion 14 of the ultrasound probe 10 over an area of interest. The image(s) 22 taken along the image plane 20 of the probe 10 are provided to an imaging system 8 and output to a display 6. The probe 10 may acquire plurality of individual images 22a-22nn while being rotated over the area of interest. See FIGS. 2A-B. See FIG. 2A. Initially, such images may be in a polar or cylindrical coordinate system. In such an instance, it may be beneficial for processing to translate these images 22a-22nn into a rectangular coordinate system. In any case, 2-D images 22a-22nn may be combined to generate a 3-D image 24. See FIG. 2B.

As shown in FIG. 1A, the ultrasound probe 10 is a side-fire probe that generates ultrasound waves out of the side surface (e.g., acquisition axis) of its acquisition portion 14. However, other imaging devices (e.g., end-fire probes) may be used in other embodiments. The illustrated system generates a series of images 22a-22nn of the prostate 12 while the probe 10 is positioned relative to the prostate. If there is little or no movement between acquisition of the images, these images may be readily registered together to generate a 3D image. However, manual manipulation of the probe 10 often results in relative and unaccounted movement between the probe 10 and the prostate 12 between subsequent images. Accordingly, it is desirable to minimize relative movement between the probe 10 and the prostrate 12 (i.e., precession, wobble or any other rotational movement of the probe about a fixed axis for image acquisition). It is also often desirable for probe 10 to remain fixed relative to the prostrate 12 during biopsy or other treatment procedures such that the desired tissue locations may be targeted accurately. To achieve such fixed positioning of probe 10, it is desirable to interface the probe 10 with a positioning device such as the exemplary positioning device 100 shown in FIG. 1B.

The positioning device 100 maintains the probe 10 in a fixed position relative to the patient (e.g., prostate) and provides location information (e.g., frame of reference information) for use with an acquired image. In this regard, location outputs from the positioning device 100 may be supplied to a computer and/or imaging device. Likewise, the output of the probe 10 may be provided to the computer and/or imaging device, and the computer and/or imaging device may utilize this information to more accurately register the images and output (e.g., display) of the imaged object (e.g., prostate). One exemplary positioning device is set forth in International Application Number PCT/CA2007/001076, entitled Apparatus for Guiding a Medical Tool. Another is set forth in U.S. Pat. No. 7,832,114, entitled Tracker Holder Assembly, the contents of which are fully incorporated herein by reference.

When attached to the positioning device 100, the probe handle is held by an arm of the device having set of position sensors. These position sensors are connected to the computer of the imaging system via an embedded system interface. Hence, the computer has real-time information of the location and orientation of the probe 10 in reference to a unified rectangular or Cartesian (x, y, z) coordinate system. With the dimensions of the probe 10 taken into the calculations, the 3D orientations of the 2D image planes are known. The ultrasound probe 10 sends signals to the imaging system 8, which may be connected to the same computer (e.g., via a video image grabber) as the output of the position sensors. The imaging system therefore has real-time 2D images of the scanning area in memory. The image coordinate system and the arm coordinate system are unified by a transformation. Using the acquired 2D images, a prostate surface (e.g., 3D model of the organ) may be generated and displayed on a display screen in real-time.

The computer system runs application software and computer programs which can be used to control the system components, provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

Figure 3:
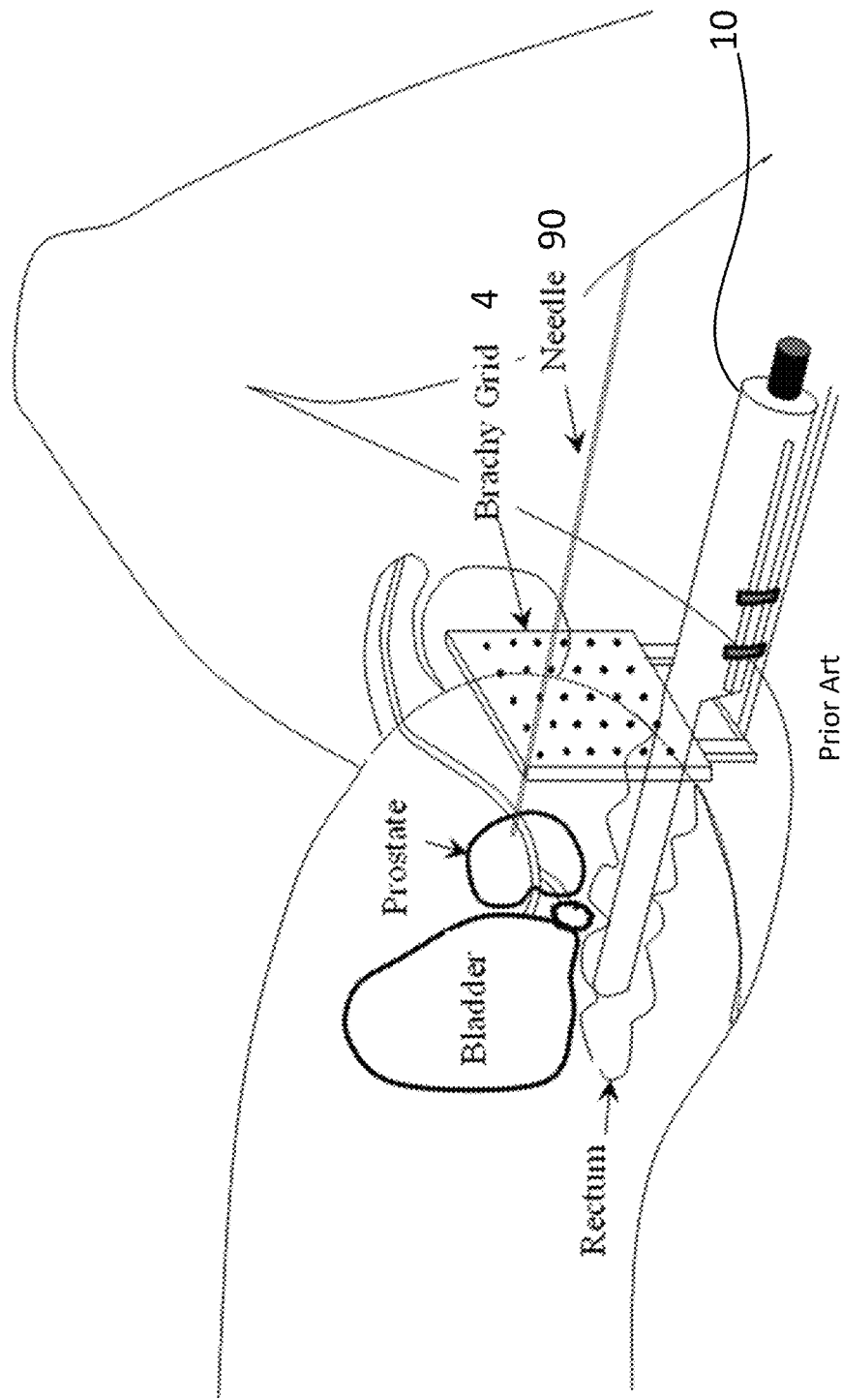
FIG. 3 illustrates a prior art biopsy and therapy solution.

The 2D and/or 3D images may be used to plan for certain interventional procedures where targeting is required (e.g., biopsy, brachytherapy seed locations, cryo-ablation locations, etc.). FIG. 3 shows a typical setup, where, with patient in lithotomic position, a side fire TRUS probe 10 is inserted into rectum of the patient while a tilting grid 4 is fixed relative to the patient. A needle 90 containing, for example, brachytherapy seeds is inserted using TRUS guidance and the needle is segmented to compute the insertion depth and deflection using live image recorded while insertion. However, the method suffers from limitations. For instance, the method uses traditional grid 4 for aligning the needle 90 with the target locations. This limits the freedom of accessing a planned location to available grid locations and may be more problematic when there are anatomical obstructions (e.g. pelvic bone).

The presented utilities overcome the limitations of prior ultrasound guided biopsy and therapy systems by providing a combined a medical imaging device holder/cradle and guidance assembly that maintains a needle trajectory of a needle or other delivery element (hereafter 'needle') held by the needle guidance assembly in a known positional relationship within an image plane of an imaging probe held by the cradle. In this regard, the needle guidance assembly may be utilized to direct a needle through a patient's perineum into the prostate to any location of interest in a current image of the probe. Thus, such targeting may be performed under real-time image guidance.

Figure 1B:
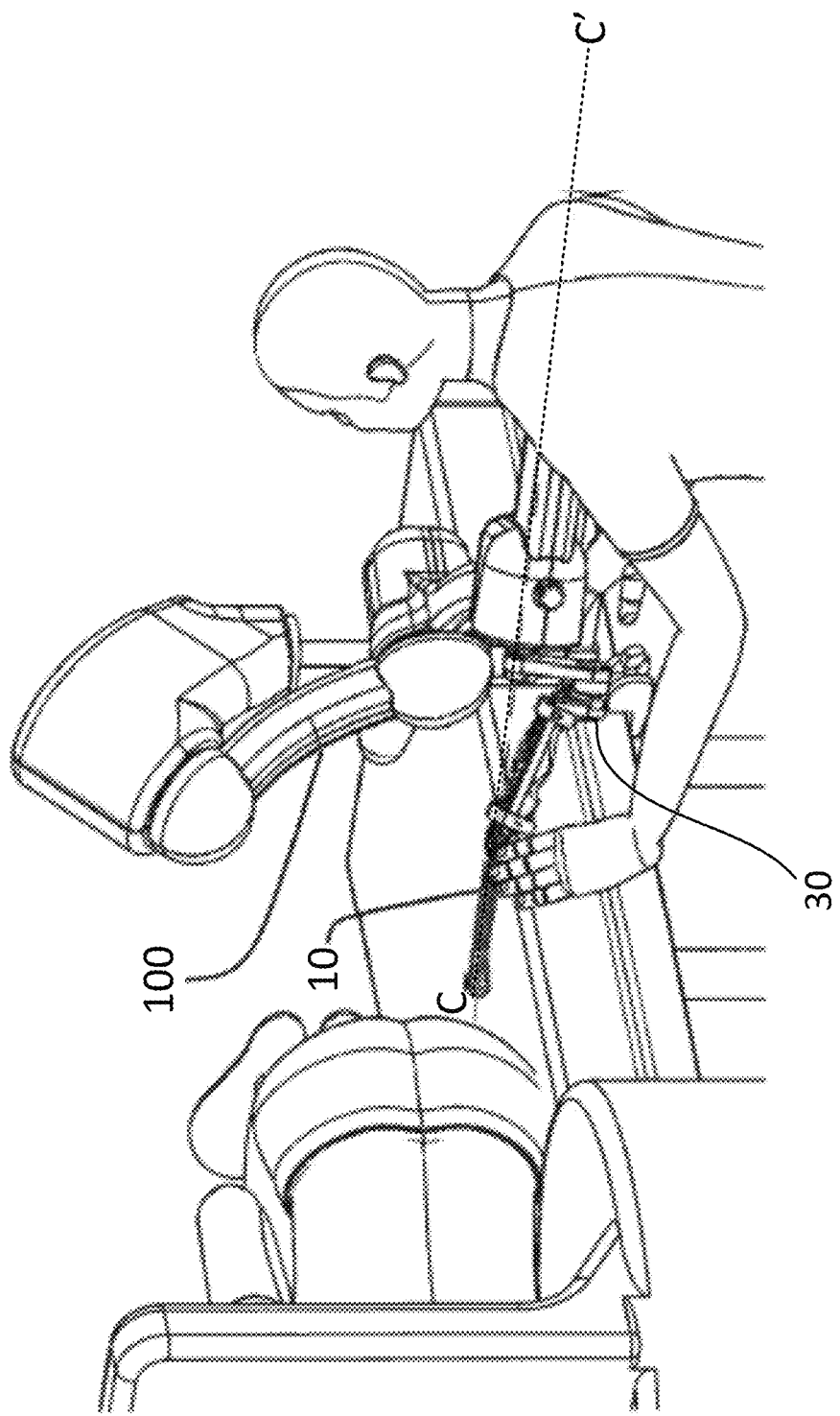
FIG. 1B illustrates use of a positioning device to position an ultrasound imaging device to perform prostate imaging.
Figure 4B:
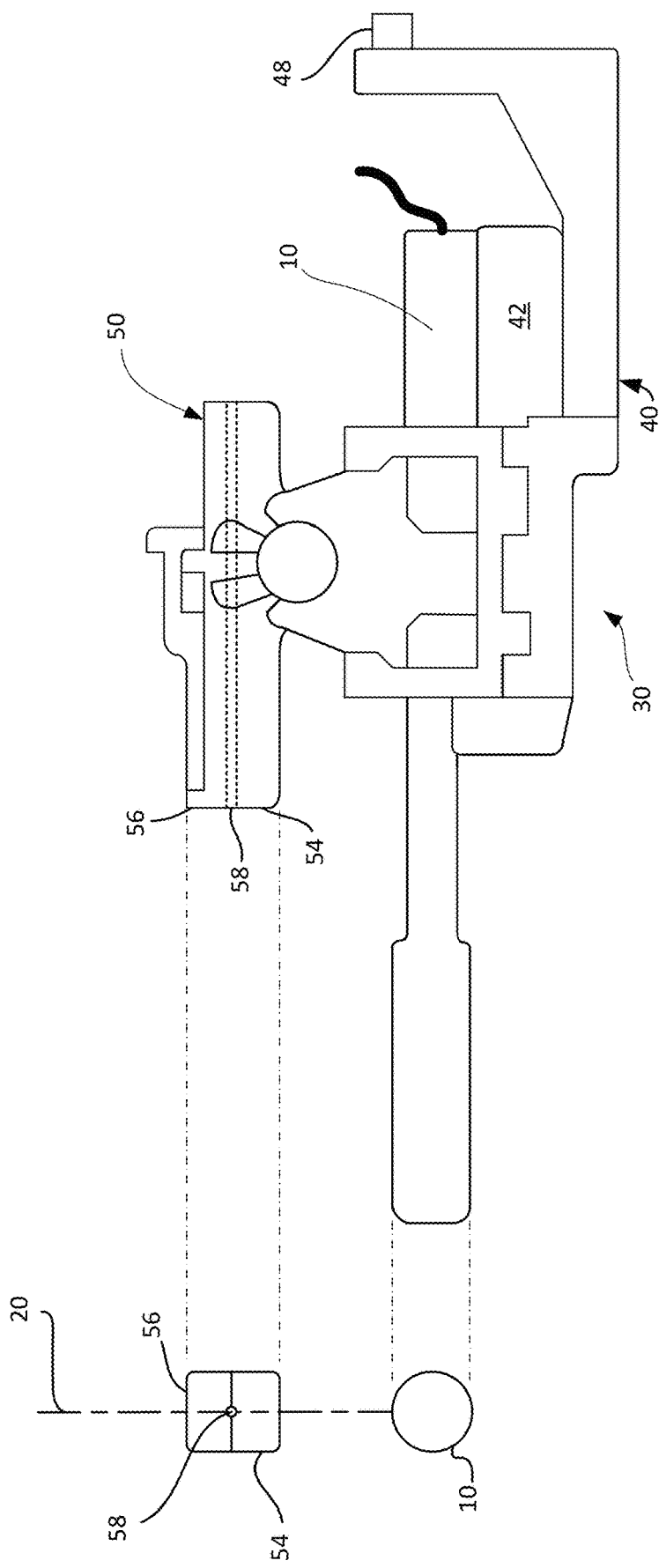
FIG. 4B illustrates alignment of a guide bore with an imaging plane with the embodiment of FIG. 4A.

FIG. 4A illustrates one embodiment of the combined a medical imaging device holder/probe holder and needle guidance assembly (hereafter 'NGA cradle'). The NGA cradle 30 interfaces an ultrasound probe 10 with a positioning device 100 (FIG. 1B). In the illustrated embodiment, the probe 10 includes an acquisition portion 14 defining an acquisition axis A-A'. The probe 10 also includes a handle portion 16 having a second length and a second diameter. Generally, the acquisition axis A-A' and the handle are offset such that they are nonaligned. The dimensions (e.g., lengths and/or diameters) of any or all of these components may vary between probes of different manufactures. FIG. 4B illustrates the ultrasound probe 10 as secured within the NGA cradle 30. While the NGA cradle 30 is described in conjunction with the positioning device 100 of FIG. 1B, it should be appreciated that the NGA cradle may be used with any appropriate positioning device.

In the illustrated embodiment, the NGA cradle 30 includes probe holder 40 having a recessed socket 42 that is sized to receive a handle portion 16 of the probe 10. See FIGS. 4A and 4B. Once the handle 16 of the probe 10 is located in the socket 42, the acquisition end 14 of the probe 10 extends beyond the distal end of the NGA cradle 30 such that it may be inserted into a rectum of a patient. In the illustrated embodiment, the probe holder 40 includes a hinged clamp 44 that is connected to a first lateral edge of the recessed socket 42 via a plurality of mating knuckles 46, 47. A hinge pin (not shown) extends though these knuckles. An opposing edge of the clamp 44 includes a latch (not shown) that allows for fixed attachment to an opposing later edge of the socket 42. In use, the clamp 44 is rotated open such that the handle 16 may be disposed within the socket 42. At this time, the clamp 44 is rotated to a closed position and secured. This secures the probe 10 within the socket 42. See FIG. 4B.

The socket 42 is a recessed surface that, in the present embodiment, is correspondingly shaped to the handle portion 16 of the ultrasound probe 10 such that the probe 10 may be disposed within the socket 42. Ultrasound probes from different OEMs may have differing shapes. In this regard, the socket 42 may include a deformable lining that allows for engaging differently configured probes. Alternatively, different sockets may be utilized for different probes. That is, the socket may be removably connected (e.g., via bolts or screws) to the NGA cradle 30 to allow matching a particular socket to a particular probe. In any arrangement, the acquisition axis A-A' of the probe 10 may be aligned with a rotational axis C-C' of the positioning device. See FIGS. 1B and 5. That is, the NGA cradle 30 preferably, but not necessarily, interfaces with the positioning device 100 such that an acquisition axis A-A' of the probe 10 is aligned with a rotational axis C-C' of the positioning device 100. This allows the acquisition portion 14 of the probe to rotate about a known fixed axis. Further, encoders of the positioning device 100 provide 3D location information allowing an image plane 20 of the probe 10 to be identified in a 3D space. In the illustrated embodiment, the NGA cradle 30 is connectable with the positioning device via a rotatable coupling 48 disposed at a proximal end of the NGA cradle 30. See FIGS. 4A, 4B and 5. This rotatable coupling 48 attaches to an arm of the positioning device and allows the NGA cradle and supported probe to rotate.

In addition to supporting probe holder 40, the NGA cradle 30 also includes a guidance assembly 50, which in the current embodiment is fixedly connected to the clamp 44 which maintains the probe 10 within the socket 42. The guidance assembly may be attached to other locations of the NGA cradle in other embodiments. As shown, the needle guide assembly 50 is connected to an upper portion of the clamp 44 via an axle or spindle 52. The spindle 52 is received within a journal formed in the clamp 44. The spindle 52 also connects to an internal journal (not shown) in a lower plate 54 of the guidance assembly 50. The spindle 52 permits the lower plate 54 of the guidance assembly 50 to rotate angularly relative to the socket 42 of the probe holder 40 and supported probe 10. In one embodiment, the guidance assembly 50 rotates about an axis (e.g., center of spindle 52) that is transverse to an imaging plane of the imaging device and/or the rotational axis of the positioning device. In such an embodiment, movement of the guidance assembly 50 and bore 58 is limited to one-degree of freedom within the imaging plane. Though discussed as using a spindle and journal, any hinged connection between the needle guide assembly and probe holder may be utilized. Removably connected to the lower plate 54 is a top cap 56. Collectively, the lower plate and top cap define a needle guide having a needle bore 58. The bore 58 of the guidance assembly 50 is sized to receive a needle such that the needle may selectively extend through the guidance assembly 50. The bore 58 of the needle guide may be designed for different gauges of interventional needles or therapy devices. Likewise, the lower plate and/or top plate may be exchanged to accommodate different needles or therapy devices. In any case, a needle/therapy device may be displaced through a distal forward surface of the needle guide assembly 50.

The NGA cradle 30 is designed such that the axis defined by the bore 58 of the guide assembly 50 is aligned with the image plane of the supported probe 10. For instance, when a side fire ultrasound probe 10 is utilized, a needle extending through the needle guide 58 will extend into the image plane 20 of the ultrasound probe 10. That is, an axis or trajectory of the bore 58 is vertically aligned with the image plane 20 of the probe 10 as illustrated by the projection of the forward ends of the guide assembly 50 and probe 10. See FIG. 4B.

Figure 5:
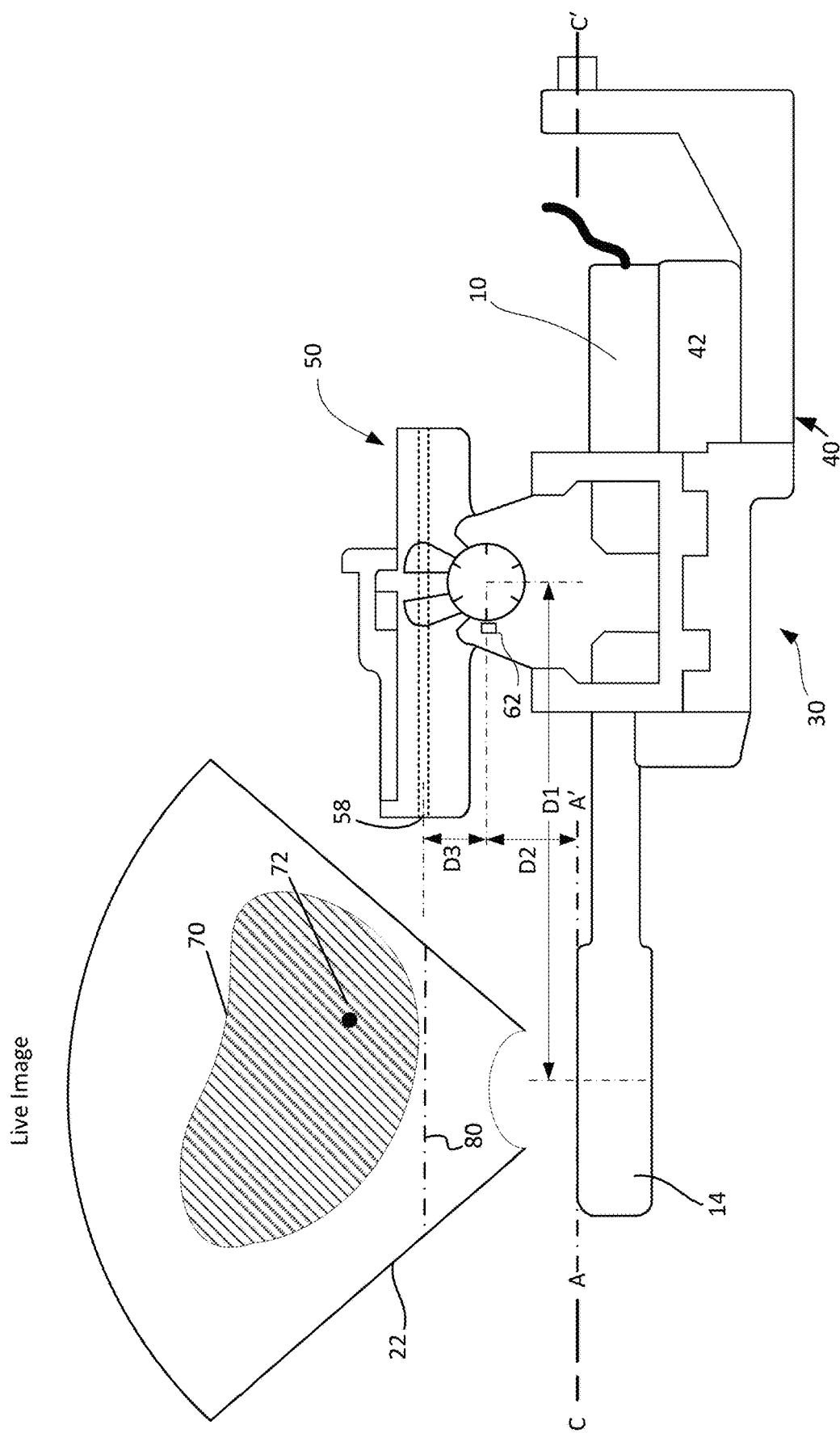
FIG. 5 illustrates the ultrasound probe of FIG. 4 disposed within the probe holder and needle guidance assembly.

Referring to FIG. 5, an exemplary image 22 of the ultrasound probe 10 as taken along the imaging plane is shown in relation to the NGA cradle 30. As will be appreciated, in use, the live video or image 22 will be output on a display device. However, this image is shown in relation to the NGA cradle 30 for purposes of discussion. Rotational encoders 62 are connected to the spindle 52 such that the angular orientation of the lower plate 52 and bore 58 relative to the remainder of the NGA cradle 30 is known. That is, outputs from such encoders 62 may be provided to the computer for integration onto the software to display the axis of the bore or needle trajectory 80 on the image 22 provided by the probe 10.

During use for a prostate procedure, the ultrasound probe 10 may generate an image 22 of a patient's prostate 70. Further, due to the use of the encoders 62 between the lower plate 54 of the guidance assembly 50 and the socket 42, a needle trajectory 80 corresponding with an axis of the bore 58 may be calculated and displayed on the ultrasound image 22. That is, the known orientation of the guidance assembly 50 relative to the imaging plane of the ultrasound probe 10 allows for determining where a needle extending through the bore 58 of the guidance assembly 50 will enter into the image 22.

If there is a desired target site 72 within the image 22 (e.g., within the prostate 70), the angular orientation Θ of the guidance assembly 50 may be adjusted about the spindle 52 (i.e., relative to the remainder of the NGA cradle 30) until the needle trajectory 80 intersects the target site. This is illustrated in FIG. 6. That is, as the angular orientation Θ of the guidance assembly 50 is adjusted, the trajectory 80 displayed on the image 22 may be likewise adjusted. The angular orientation Θ of the guidance assembly 50 may be manually adjusted in one embodiment. In further embodiments, the angular orientation of the guidance assembly may be robotically controlled. That is, various motors or other actuators may be utilized to align the needle trajectory with the planned target site. In a further arrangement, the user may select a target site 72 on the ultrasound image 22 (e.g., via a touch screen or other user input) and the guidance assembly 50 may automatically align the trajectory 80 with the user selected target site 72.

FIGS. 7 and 8 illustrate the disposition of a needle 90 (biopsy needle, therapy needle etc.) through the bore 58 of the guidance assembly 50. As will be appreciated, the needle 90 may be disposed within the bore 58 of the needle guidance assembly 50 prior to angular adjustment of the guidance assembly. In any case, once the bore 58 of the guidance assembly 50 is aligned so the needle trajectory 80 extends through the target site 72, the needle 90 may be advanced into the prostate to the target site. As the needle 90 is disposed within the imaging plane of the ultrasound probe 10, the advancement of the needle 90 into the prostate may be monitored in real time. See FIG. 8. Once a biopsy is taken or therapy is applied to the target site, additional target sites may be biopsied and/or treated. This may entail rotating the NGA cradle 30 to align the image plane with another target site. If necessary, the initial needle 90 may be removed from the needle guide assembly 50 and replaced with another needle. That is, the top 56 may be removed from the lower plate 54 to allow removal of the initial needle and replacement with an additional needle. Other configurations are possible.

Figure 9A:
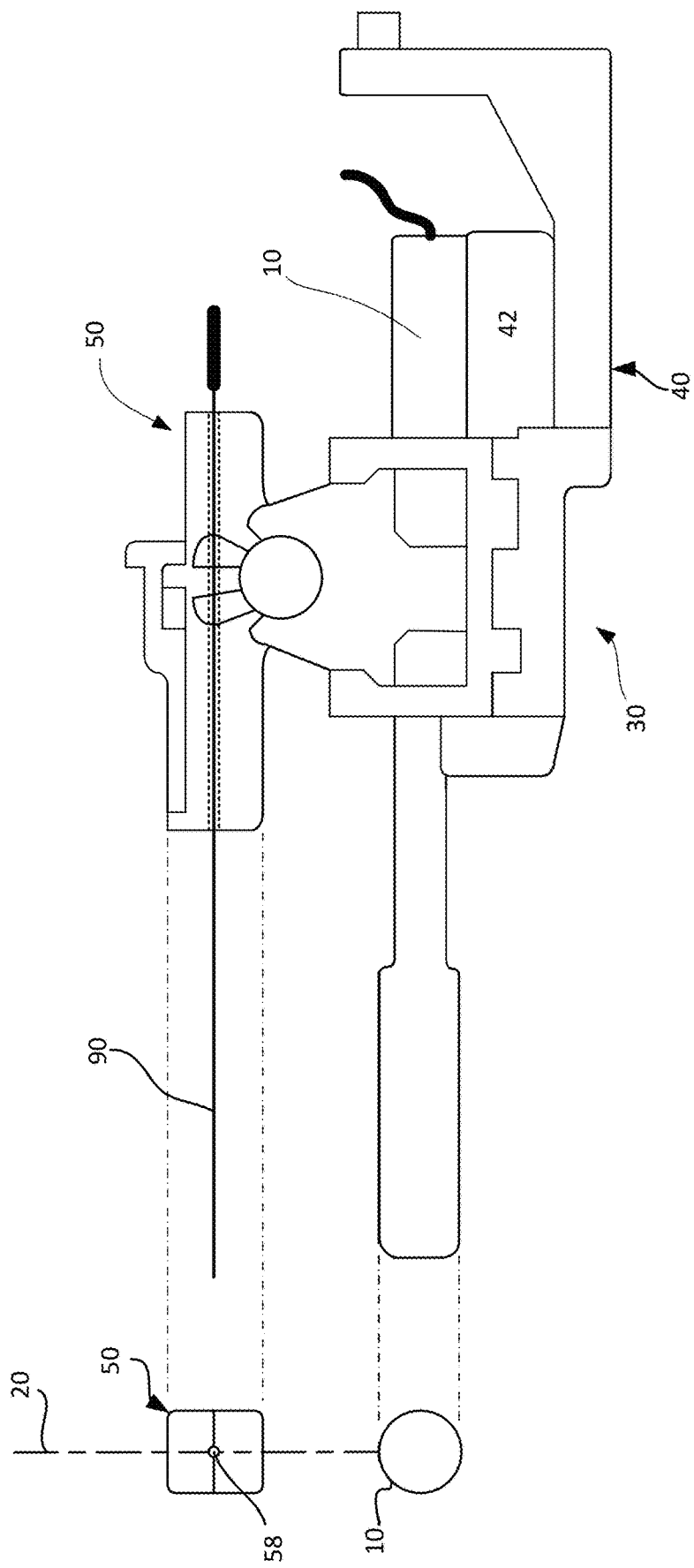
FIG. 9A illustrate insertion of a needle in the needle guidance assembly for calibration.
Figure 10B:
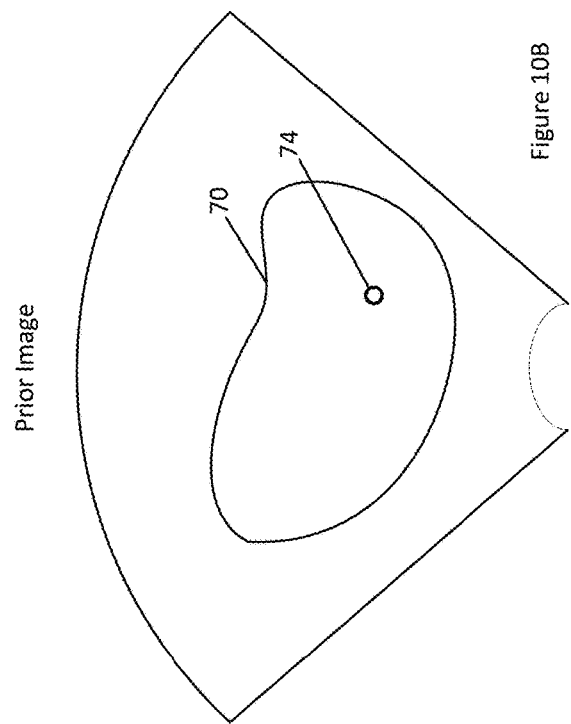
FIGS. 10A-10D illustrate registration of information from a prior image with a current image.
Figure 10D:
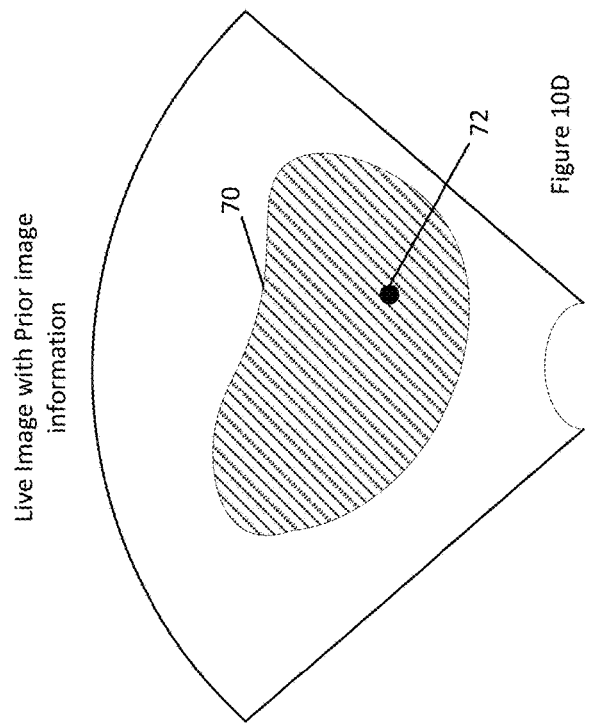
Figure 10A:
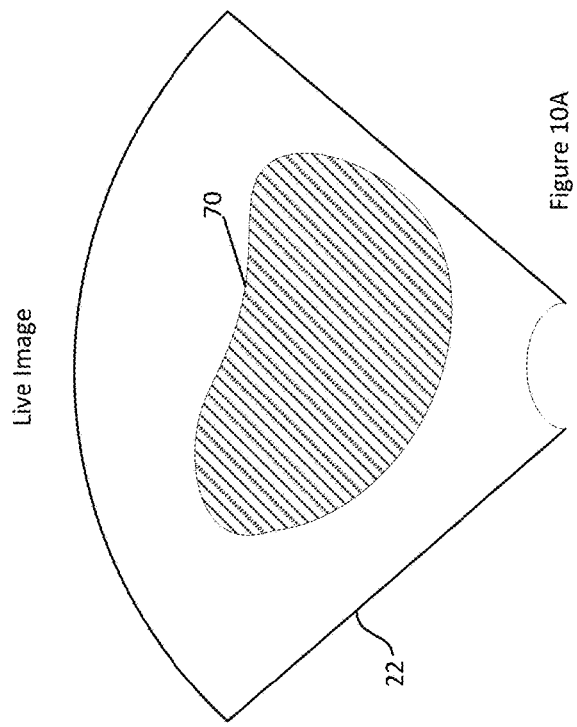
Figure 10C:
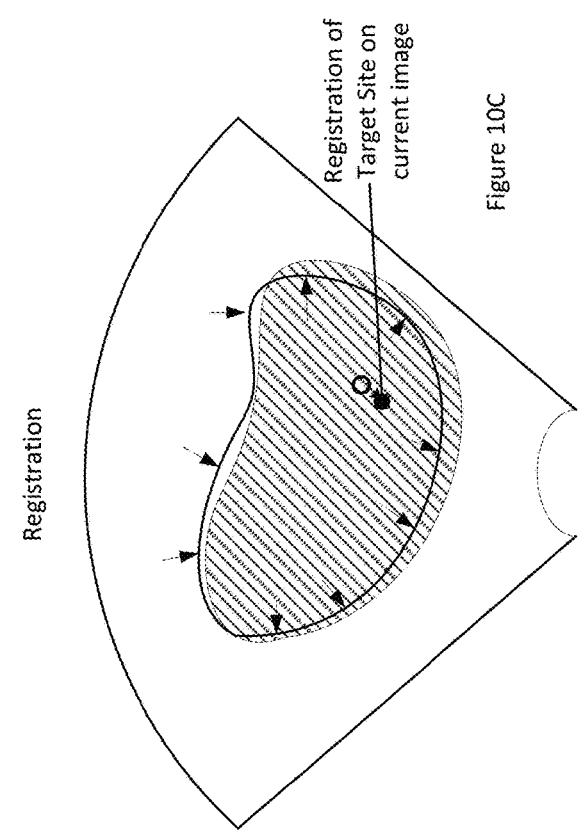

In order to utilize the NGA cradle 30 with an imaging system, the probe, cradle and needle guide assembly 50 must initially be calibrated. Initially, this requires placement of the probe within the socket 42 of the cradle such that the trajectory of the bore 58 defined by the guidance assembly is within the imaging plane 20 of the probe 10. See FIGS. 9A-9D. In one arrangement, a needle 90 may be extended through the bore 58 of the guidance assembly 50 and the probe 10 may generate an image after being secured within the socket 42. The orientation of the probe 10 within the socket may be adjusted (FIGS. 9B and 9C) until the needle 90 is disposed within the image 22. See FIG. 9D. At this time, the clamp 44 may be closed to secure the probe 10 within the cradle socket 42 fixing the position of the imaging plane with the bore 58 of the guidance assembly. In other arrangements, the tolerance of the socket 42 may be such that the image plane 20 of a specific known probe is necessarily aligned with the bore 58 of the guidance assembly 50. In any arrangement, once the image plane 20 of the probe 10 is aligned with the bore 58 of the guidance assembly 50, the angular orientation of the guidance assembly may be calibrated. This requires knowing the value of the encoder 62 when the needle guide assembly 50 is parallel (or in another known orientation) with the acquisition axis A-A' of the probe. This is illustrated in FIG. 5. As shown, when the bore 58 of the guidance assembly 80 is parallel with the acquisition axis A-A' of the probe, the distances: D1, between the center of the ultrasound transducer (e.g., acquisition portion 14 of the probe 10) and the spindle axis of the guidance assembly 50; D2, between the spindle axis of the guidance assembly 50 and acquisition axis A-A' of the probe 10; and D3, between the spindle axis of the needle guidance assembly 50 and the bore 58 of the guidance assembly 50, are known. The value of the encoder 62 at this position may be a 'null' reference. Accordingly, any angular offset registered by the encoder 62 thereafter can be utilized to plot the trajectory 80 of the bore 58 of the guidance assembly the image 22 of the probe 10 using basic geometry.

Another important feature of the presented system is the ability to register prior acquired images with a current image of the supported imaging probe. That is, the system may include a medical imaging registration system that allows a first medical image (ultrasound image) of a tissue area acquired at a first time (e.g., prior image) to be registered with a second medical image of a tissue area of interest that is acquired at a second subsequent time (e.g., real-time ultrasound image). Once the prior image is registered to the real-time image, information associated with the prior image may be transferred to/displayed on the real-time image for treatment purposes. Such a registration system is disclosed in U.S. Patent Publication No 2008/0161687 the entire contents of which is incorporated herein by reference.

Registration of prior images with a current image may be beneficial in a number of instances. For instance, a patient may have biopsy cores taken during an initial visit and a lab may subsequently analyze those biopsy cores and register that information to the original/prior image. For instance, histological or pathological information for the biopsy core may be determined and registered to its actual location in the prior image. By way of example and not limitation, in urologic pathology, high-grade prostatic intraepithelial neoplasia, abbreviated HGPIN, is an abnormality of prostatic glands and believed to precede the development of prostate adenocarcinoma (the most common form of prostate cancer). The biopsy cores may be scored for this and/or other carcinogenic markers. At a subsequent visit, the prior image and biopsy information may be registered to the real-time image for therapy purposes. Stated otherwise, target sites 72 within a current image may be generated based on information acquired from prior images. Such registration is graphically illustrated on FIGS. 10A-10D.

As shown, during a procedure, a live image 22 of a patient prostate 70 may be obtained. See FIG. 10A. A prior image 122, which includes one or more previous biopsy sites or regions of interest mapped to the prior image 122 is obtained (e.g., from imaging system memory). See FIG. 10B. Such biopsy sites or regions of interest may define target sites for a current procedure (e.g., therapy). However, in the case of soft anatomical features such as the prostate, the shape of the prostate often changes slightly between imaging sessions. Further, the frame of reference of the prior image and live image may differ. Accordingly, the images are typically registered to put these images into a common frame of reference. For instance, the surface or boundary of the prostate 70 of the prior image 122 and live image 22 may be segmented such that the prior image may be elastically deformed to the frame of reference of the live image. See FIG. 10C. That is, the shape of the prostate from the live image and the shape of the prostate of the prior image do not match in shape when overlaid. Accordingly, a registration process is utilized to align the boundaries of the images 22, 122. This registration may be performed in any appropriate manner. Once the images 22, 122 are registered, the regions of interest 74 from the prior image 122 may be illustrated on the live image 22 in its proper location within the live image 22. See FIG. 10D. Accordingly, the prior region of interest 74 may define a target site 72 in the live image.

In summary, the system allows for live image guidance to targeted locations within an internal anatomical structure such as a patient's prostate. However, it will be appreciated that in addition to utilizing a 2D image, the two-dimensional image may be combined with a three-dimensional image acquired by the probe. Further, as the probe and needle guide assembly are operative to co-rotate, any location within the anatomical structure may be imaged and targeted. Further, the ability to adjust the angular position of the needle guide assembly within the plane of the ultrasound transducer likewise allows for targeting any location within the field of view of the imaging device. In prostate applications, one advantage of the angulated needle guide assembly is the ability to access anterior parts of the prostate gland located behind the pubic arch.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described above are further intended to explain best modes known of practicing the invention and to enable others skilled in the art to utilize the invention in similar or other embodiments and with various modifications required by the particular application(s) or use(s) of the present invention. It is intended that the appended claims be construed to include alternative embodiments to the extent permitted by the prior art.

What is claimed:

1. A system for diagnoses and treatment, comprising:
 a probe holder having:
   recessed surface sized to receive and secure at least a portion of an ultrasound probe such that an imaging plane of the ultrasound probe is fixed in a known orientation relative to said probe holder; and
   a rotatable coupling attached to said probe holder and configured for connection with a positioning device, wherein said rotatable coupling permits said probe holder to rotate about a first axis;
 a needle guidance assembly connected to said probe holder via a hinge that permits the needle guidance assembly to rotate relative to the probe holder about a single second axis that is transverse to the first axis, the needle guidance assembly having:
   a guide bore extending through at least a portion of said needle guidance assembly, the guide bore configured to receive an interventional needle, wherein a bore axis of said guide bore is transverse to the second axis such that it is aligned within the imaging plane of the ultrasound probe when the ultrasound probe is disposed within said probe holder, wherein rotation of the needle guidance assembly adjusts an angular orientation of a trajectory of the bore axis within the image plane; and wherein said probe holder and said needle guide assembly connected to said probe holder are configured to co-rotate about said first axis via the rotatable coupling.

2. The device of claim 1, further comprising an ultrasound probe disposed in said recessed surface, said ultrasound probe having a handle portion and an acquisition portion that generally defines an acquisition axis.

3. The device of claim 2, wherein said recessed surface of said probe holder is correspondingly shaped to said handle portion of said ultrasound probe.

4. The device of claim 3, wherein said acquisition axis of said ultrasound probe is substantially aligned with said first axis.

5. The device of claim 2, wherein said ultrasound probe is a side-fire ultrasound probe.

6. The device of claim 1, further comprising:
at least one encoder configured to generate an output indicative of an angular orientation of said needle guidance assembly relative to said probe holder.

7. The device of claim 6, further comprising:
an imaging system, wherein said imaging system is configured to display an image corresponding to the image plane and plot a trajectory of said bore axis of said guide bore on said image based on said output of said at least one encoder.

8. The device of claim 7, wherein said imaging system is configured to receive positional information from the positioning device.

9. The device of claim 8, wherein said imaging system is configured to receive multiple 2D images from said ultrasound probe and generate a 3D image from said 2D images, wherein said 2D images are angularly offset about said first axis.

10. The device of claim 1, wherein said guide bore is sized to receive a biopsy needle configured to extract tissue samples.

11. The device of claim 1, wherein said guide bore is sized to receive an interventional needle configured to apply therapeutic matter.

12. The device of claim 11, wherein said therapeutic matter comprises at least one of:
brachytherapy seeds;
a cryoablation fluid;
ablation energy; and
electroporation energy.

13. The device of claim 1, wherein said needle guidance assembly further comprises:
a lower member connected to said hinge; and
an upper member connectable to said lower member, wherein said lower member and said upper member collectively define said guide bore when said upper member is connected to said lower member.

14. A method of administering treatment, comprising:
scanning a patient with an internally positioned imaging probe disposed within a probe holder that supports the imaging probe such that an orientation of a two-dimensional image plane of said imaging probe is known;
displaying, on a display, a three-dimensional image of patient tissue generated by a set of two-dimensional image planes acquired by the imaging probe;
co-rotating the probe holder and a connected needle guidance assembly having a guide bore about a common first axis via a rotatable coupling until a target site within said three-dimensional image is within a current image plane of the imaging probe, wherein said needle guidance assembly is hingedly attached to said probe holder to permit the needle guidance assembly to rotate relative to the probe holder about a second axis that is transverse to the first axis, and wherein a guide bore axis said needle guide bore is aligned with said current image plane of said imaging probe;
plotting a trajectory axis of said guide bore axis on said current image plane;
adjusting an angular orientation of said needle guide assembly relative to said probe holder about said second axis until said trajectory axis of said needle guide bore is aligned with said target site; and
extending an interventional needle through said needle guide bore into the patient tissue to said target site.

15. The method of claim 14, further comprising:
displaying penetration of said interventional needle on said image as said interventional needle extends into patient tissue.

16. The method of claim 14, further comprising:
receiving an output of a positional encoder disposed between the probe holder and the needle guide assembly;
calculating the trajectory axis of the guide bore of the guide assembly based upon the output of the encoder; and
overlaying a trajectory line on the current image plane, wherein the trajectory line identifies an insertion a path of the interventional needle.

* * * * *